United States Patent
Hasegawa et al.

(10) Patent No.: US 7,217,829 B2
(45) Date of Patent: May 15, 2007

(54) ZINC ACRYLATE AND METHOD FOR PRODUCTION THEREOF

(75) Inventors: Manabu Hasegawa, Tokyo (JP); Yoshinori Saito, Chiba (JP)

(73) Assignee: Nippon Shokubai Co., Ltd., Osaka (JP)

( * ) Notice: Subject to any disclaimer, the term of this patent is extended or adjusted under 35 U.S.C. 154(b) by 225 days.

(21) Appl. No.: 11/115,914

(22) Filed: Apr. 27, 2005

(65) Prior Publication Data

US 2005/0187397 A1 Aug. 25, 2005

Related U.S. Application Data

(62) Division of application No. 10/705,650, filed on Nov. 10, 2003, now abandoned.

(30) Foreign Application Priority Data

Nov. 11, 2002 (JP) ............................. 2002-327496

(51) Int. Cl.
*C07F 3/06* (2006.01)
(52) U.S. Cl. ..................................... 556/131
(58) Field of Classification Search ................. 556/131
See application file for complete search history.

(56) References Cited

U.S. PATENT DOCUMENTS 4,169,599 A 10/1979 Fujio et al. ................. 273/220
5,789,616 A 8/1998 Kobayashi et al. ......... 562/598
6,278,010 B1* 8/2001 Tsou et al. .................. 556/131
6,956,128 B2 10/2005 Higuchi et al.

FOREIGN PATENT DOCUMENTS

| GB | 1595477 | 12/1977 |
|---|---|---|
| GB | 2 124 221 A | 2/1984 |
| JP | A-52-154436 | 12/1977 |
| JP | A-53-083834 | 7/1978 |
| JP | B-58-014416 | 3/1983 |
| JP | A-02-218639 | 5/1985 |
| JP | A-60-094434 | 5/1985 |
| JP | 01-038744 | 2/1989 |
| JP | 08-012200 | 1/1996 |
| JP | A-09-202747 | 8/1997 |

* cited by examiner

*Primary Examiner*—Porfirio Nazario-Gonzalez
(74) *Attorney, Agent, or Firm*—Mathews, Shepherd, et al.

(57) ABSTRACT

Zinc acrylate excelling in flowability is provided. It is produced by a method, characterized by dispersing zinc oxide in any of (a) an aliphatic hydrocarbon solvent, (b) a mixed solvent formed between an aliphatic hydrocarbon solvent and an aromatic hydrocarbon solvent, and (c) a mixed solvent formed between an aromatic hydrocarbon solvent and an alcohol and causing acrylic acid to react with said zinc oxide in said solvent. The obtained zinc acrylate refrains from undergoing secondary aggregation, excels in disintegrability and, when kneaded in a rubber composition, exhibits excellent dispersibility.

4 Claims, 4 Drawing Sheets

ZINC ACRYLATE AND METHOD FOR PRODUCTION THEREOF

CROSS REFERENCE TO RELATED APPLICATION

This application is a divisional application of U.S. patent application Ser. No. 10/705,650, filed Nov. 10, 2003, now abandoned, the entirety of which is hereby incorporated by reference into this application.

BACKGROUND OF THE INVENTION

1. Field of the Invention

This invention relates to a method for the production of zinc acrylate by the reaction of acrylic acid and zinc oxide by virtue of the use of a specific mixed solvent and more particularly to a method for the production of zinc acrylate which enables the crystal form of zinc acrylate to be adjusted owing to the use of the specific mixed solvent.

2. Description of the Related Art

Zinc acrylate is a useful compound as a cross-linking agent and is used as added in rubber composition to improve the vulcanizability or used as a modifier for a varying synthetic resin.

As a means to obtain zinc acrylate, a method which comprises inducing acrylic acid to react with a zinc compound in an organic solvent, distilling the reaction solution to expel the organic solvent, and thereafter drying the residue of the distillation (JP-B-58-14416) and a method which comprises filtering the reaction solution to remove the organic solvent and thereafter drying the residue of the filtration have been available. These methods, however, are deficient in workability because their reaction products stick tenaciously to the inner walls of their reaction vessels and to the agitating elements or aggregate into clusters. When the solvent is removed by decompression, the solvent contained in the produced zinc acrylate is scattered and the produced zinc acrylate is partly scattered as well to lower the yield thereof and the economy of the production is heavily impaired because the decomposition necessitates installation of extra devices for separation and recovery, for example.

For the sake of using zinc acrylate by kneading it in a rubber composition, numerous methods for coating the surface of zinc acrylate particles by the addition of a higher fatty acid such as stearic acid or a zinc salt thereof have been proposed (JP-A-52-154436, JP-A-53-83834, JP-60-94434, and JP-A-02-218639).

These methods, however, necessitate incorporation of a step for coating the surface of particles of zinc acrylate by the addition of such a high fatty acid as stearic acid or a zinc salt thereof besides a step for effecting the reaction of acrylic acid with a zinc compound and installation of devices appropriate for such steps. Further, for the purpose of enabling the produced zinc acrylate to be kneaded in a rubber composition, it is required to be an impalpable powder having a particle size of not more than 325 mesh (44 µm). Thus, these methods further necessitate a step for pulverizing the produced zinc acrylate into an impalpable powder. This step of pulverization not only calls for a huge labor but also entails the possibility of deteriorating the working atmosphere and inducing the problem of hygiene because zinc acrylate is unusually liable to emit dust during and after the work of pulverization.

A method which produces zinc acrylate by using toluene as a reaction solvent in the presence of an anionic surfactant, adding acrylic acid and a higher fatty acid of 12 to 30 carbon atoms thereto while dispersing zinc oxide therein, causing the zinc oxide to react with the acrylic acid, and adding the product of this reaction to the organic solvent has been also available. This method can produce fine zinc acrylate. The produced zinc acrylate, when kneaded in a rubber composition, very rarely induces cohesion and aggregation, disperses uniformly, and brings the kneading to completion (Official gazette of JP-A-09-202747).

When the higher fatty acid is reacted with acrylic acid in the toluene which has zinc oxide dispersed therein, the product aimed at must be dried after it has been separated from the organic solvent because the reaction generates water of constitution. The produced zinc acrylate is possibly aggregated during the course of this drying. For the process of producing zinc acrylate, the step of pulverization is indispensable because the presence of aggregated clusters results in degrading the dispersibility.

The samples of zinc acrylate produced in Examples 1–4 inserted in the official gazette of JP-A-09-202747 invariably contain particles exceeding 500 µm in diameter in proportions exceeding 20% by weight of the whole particles and, in their unaltered form, entail a disadvantage in failing to be smoothly kneaded or satisfactorily dispersed without producing aggregated clusters in rubber. They contain zinc acrylate particles of diameters not more than 5 µm in proportions in the range of 40–43% by weight while they contain the same particles of a diameter of not more than 44 µm in proportions in the range of 63–66% by weight. This fact indicates that the step of pulverization is indispensable to the production of fine particles of zinc acrylate possessing a fine and uniform particle diameter. Thus, the desirability of developing zinc acrylate which can be smoothly kneaded in a rubber composition and manifests satisfactory dispersibility thereto has been commanding strong general recognition. The methods known to the art, however, fall short of fulfilling the demand.

The produced zinc acrylate, for the sake of ensuring safe transportation and storage, is expected to avoid incurring repeated aggregation even during a protracted storage and, for the sake of facilitating transportation and storage, is expected to possess as high build density as permissible. The conventional products of zinc acrylate, however, are liable to incur aggregation during storage and this aggregation constitutes one cause for degrading the flowability of the compound at the time of use.

Regarding the process for the production of zinc acrylate, while the adhesion of the reaction product to the inner wall of the reaction vessel and to the agitation element mentioned above has entailed such problems as degrading the workability and jeopardizing the economy of the production, the problems have not been satisfactorily coped with.

SUMMARY OF THE INVENTION

The present inventor has made a deliberate study of crystals of zinc acrylate formed in the reaction solution and crystals of zinc acrylate obtained after drying and has consequently found that the crystals of the zinc acrylate taken out of the reaction solution and then dried differ in shape from the crystals of the zinc acrylate held in the reaction solution and that the crystals of zinc acrylate in the reaction solution have the shape and size thereof varied with the kind of the organic solvent which is used as the reaction solvent for zinc acrylate. This invention has been perfected as a result.

Specifically, this invention is aimed at providing a method for the production of zinc acrylate which comprises dispersing zinc oxide in any of (a) an aliphatic hydrocarbon solvent, (b) a mixed solvent formed between an aliphatic hydrocarbon solvent and an aromatic hydrocarbon solvent, and (c) a mixed solvent formed between an aromatic hydrocarbon solvent and an alcohol and causing the zinc oxide to react with acrylic acid in the solvent. By finding that the crystal form of zinc acrylate varies with the kind of reaction solvent and the degree of interfacial surface tension of a solvent to water and adjusting the interfacial surface tension of the reaction solvent to water, it is made possible to control the crystal form of zinc acrylate and produce zinc acrylate excelling in flowability.

This invention is also aimed at providing zinc acrylate the crystals of which have a long axis of not less than 5 µm and an aspect ratio in the range of 1–30. By finding that the degree of secondary aggregation is varied with the crystal size of zinc acrylate and selecting the crystal size of zinc acrylate specified above, it is made possible to repress the secondary aggregation and secure easily the flowability necessary for excelling in collapsibleness.

This invention is further aimed at providing a zinc acrylate composition which comprises the zinc acrylate mentioned above and a zinc salt of a higher fatty acid of 12–30 carbon atoms. The zinc salt of higher fatty acid is added in the composition as a fluidity retaining agent. The composition, even when kneaded in a rubber composition, is capable of securing necessary dispersibility.

According to the method contemplated by this invention for the production of zinc acrylate, the crystal form of zinc acrylate to be obtained can be adjusted by varying the kind of a reaction solvent to be used. The crystals of zinc acrylate vary their flowability and fixability with their crystal form. In this invention, the zinc acrylate to be produced is enabled to secure the flowability aimed at by changing the kind of a reaction solvent thereby adjusting the crystal form. The zinc acrylate produced by this invention is restrained from forming secondary aggregation and, even when their crystals are mutually bound, is enabled to disintegrate the bound crystals and regain flowability. When the zinc acrylate is kneaded as a vulcanizer as in a rubber composition, it is enabled to serve as a species of zinc acrylate excelling in dispersibility.

DESCRIPTION OF THE PREFERRED EMBODIMENTS

Figure 1:
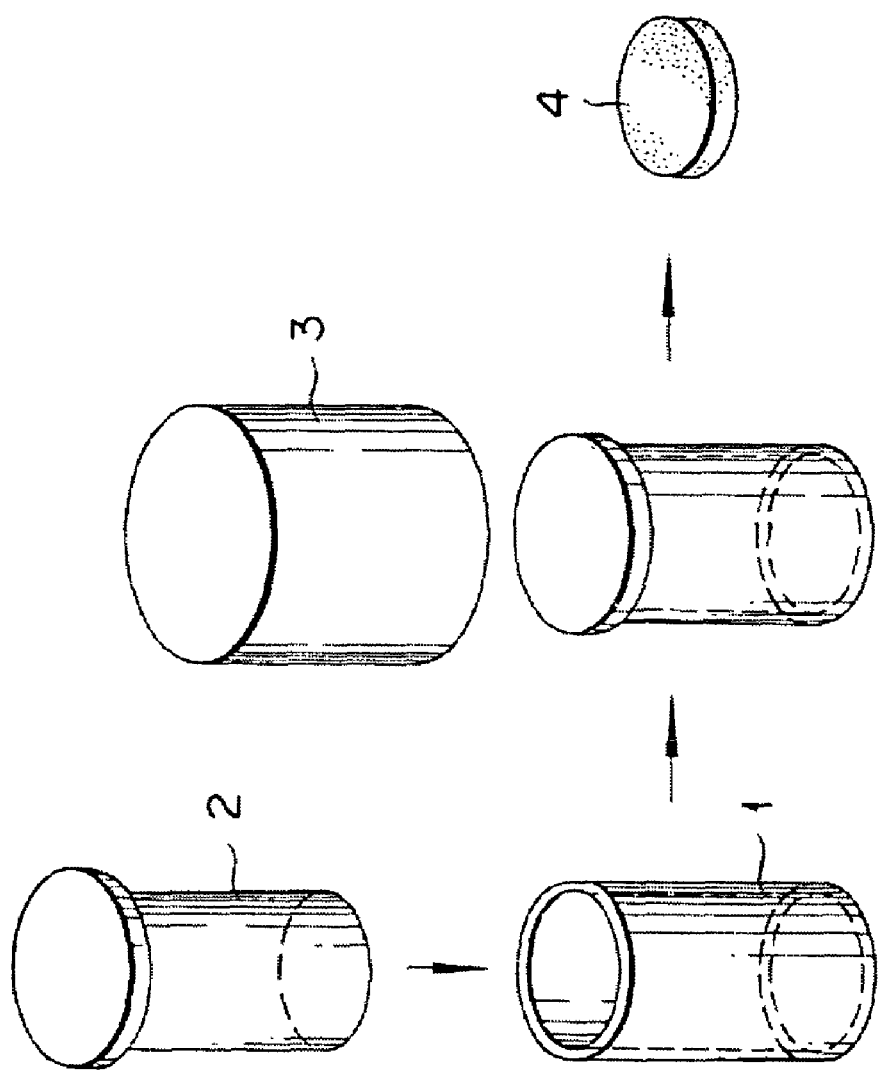
FIG. 1 is a diagram illustrating a method for determining a solid disintegrating load of sample zinc acrylate produced in working examples and comparative examples.

The first aspect of this invention is directed toward a method for the production of zinc acrylate, which comprises dispersing zinc oxide in any of (a) an aliphatic hydrocarbon solvent, (b) a mixed solvent formed between an aliphatic hydrocarbon solvent and an aromatic hydrocarbon solvent, and (c) a mixed solvent formed between an aromatic hydrocarbon solvent and an alcohol and causing acrylic acid to react with said zinc oxide in said solvent.

As a means to produce zinc acrylate, a method which synthesizes this compound by inducing the reaction of acrylic acid and zinc oxide in toluene is generally followed. The reason for using toluene as the reaction solvent is that the water of constitution which occurs in the reaction of acrylic acid and zinc oxide as represented by the following formula can be easily eliminated by azeotropic distillation and that the reaction performed in this manner affords fine zinc acrylate.

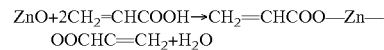

$$ZnO+2CH_2=CHCOOH \rightarrow CH_2=CHCOO-Zn-OOCHC=CH_2+H_2O$$

When the kind of reaction solvent is changed in the production of zinc acrylate, however, the crystal form of zinc acrylate in the reaction solution is varied from that of the zinc acrylate produced (a) when an aliphatic hydrocarbon solvent is used alone, (b) when a mixed solvent formed between an aliphatic hydrocarbon solvent and an aromatic hydrocarbon solvent is used, and (c) when a mixed solvent formed between an aromatic hydrocarbon solvent and an alcohol is used. This difference may be explained by a supposition that since the formation and growth of crystals of zinc acrylate mainly occurs in the water constituted by the reaction, the crystal form of zinc acrylate can be varied by varying the interfacial tension exhibited by the solvent to the water. In fact, when the solvent having an interfacial tension of 35–40 dynes/cm (20° C.) to water added to the solvent having an interfacial tension of 50–55 dynes/cm (20° C.) to water is increased, the crystals become gradually slender. In contrast, when the solvent having an interfacial tension of not more than 10 dynes/cm added to the solvent having an interfacial tension of 35–40 dynes/cm (20° C.) to water is increased, the crystals become gradually grow in bulkiness. For example, the zinc acrylate which is obtained by using toluene, one kind of aromatic hydrocarbon solvent having an interfacial tension of 36 dynes/cm (20° C.) to water assumes a slender crystal form as compared with the zinc acrylate produced with a solvent having an intefacial tension of 50–55 dynes/cm (20° C.) to water. Since the slender crystals are liable to be cut in the reaction solution, the produced zinc acrylate assumes the shape of slender crystals. This zinc acrylate tends to undergo secondary aggregation and form aggregated clusters after it is separated from the solution. Thus, the conventional zinc acrylate is actually clusters of secondary aggregation of zinc acrylate. When heptane which is one kind of aliphatic hydrocarbon solvent having an interfacial tension of 51 dynes/cm (20° C.) to water is used, the crystals extracted from the reaction solution and dried avoid undergoing secondary aggregation, though they become thicker and longer than those obtained by using toluene. As a result, the zinc acrylate at the time of actual use assumes a small particle diameter and excels in flowability, represses solidification and, when suffered to form cohering clusters, exhibits excellent disintegrability. This zinc acrylate renders the storage and transportation thereof convenient because it has a high bulk density. Thus, this invention has decided to vary the crystal form of zinc acrylate and produce zinc acrylate excelling in flowability and disintegrability by using (a) an aliphatic hydrocarbon solvent, (b) a mixed solvent formed between an aliphatic hydrocarbon solvent and an aromatic hydrocarbon solvent, and (c) a mixed solvent formed between an aromatic hydrocarbon solvent and an alcohol. Now, this invention will be described in detail below.

The aliphatic hydrocarbon solvents which are usable in this invention are cyclic or chain alkanes optionally possessing a branch of 1–14 carbon atoms such as pentane, isopentane, hexane, isohexane, heptane, isoheptane, octane, isooctane, nonane, isononane, cyclohexane, cycloheptane, cyclooctane, and cyclononane. Among other aliphataic hydrocarabon solvents mentioned above, the alkanes of 6–8 carbon atoms such as hexane, heptane, and octane are used advantageously. The reason for the preference of these alkanes is that they facilitate removal of water from the system by virtue of azeotropy. These aliphatic hydrocarbon solvents may be used either singly or in the form of a mixed solvent. Optionally, they may be used in the form of a mixed solvent using any of the aromatic hydrocarbon solvents which will be more specifically described herein below. The aliphatic hydrocarbon solvents mentioned above have interfacial tension of not more than 55 dynes/cm to water. The crystals of zinc acrylate obtained such a solvent are thicker and longer than the crystals obtained when toluene is used as the reaction solvent. The crystals in the reaction solvent, therefore, are not broken very copiously. The crystals, even after they are taken out of the reaction solvent and dried, do not cohere very much and, even when they undergo secondary aggregation, enable the coherent masses to be easily disintegrated. Further, the use of the solvent mentioned above brings such advantages of production as reducing the load exerted on the agitation element and reducing the adhesion to the reaction vessel.

The aromatic hydrocarbon solvent which has the interfacial tension of not more than 40 dynes/cm to water and is used as mixed with the aliphatic hydrocarbon solvent mentioned above is at least one member selected from the group consisting of toluene, xylene, mesitylene, cumene, cymene, styrene, benzene, and ethylbenzene. Among other aromatic hydrocarbon solvents enumerated above, toluene and xylene are used particularly advantageously. The reason for the preference of these members is that they facilitate the removal of water from the system by virtue of azeotropy. The mixing ratio of the aliphatic hydrocarbon solvent and the aromatic hydrocarbon solvent is a matter of arbitrary decision in this invention. In the light of the fact that the crystal form of zinc acrylate varies with this mixing ratio and from the point of view of restraining zinc acrylate from undergoing secondary aggregation, however, the ratio by weight of the aliphatic hydrocarbon solvent and the aromatic hydrocarbon solvent is preferably in the range of 10:0 to 6:4 and more preferably in the range of 10:0 to 8:2. Particularly, the crystal form varies with the amounts of the aromatic hydrocarbon solvent and the aliphatic hydrocarbon solvent to be incorporated; the crystals grow thick when the amount of such an aliphatic hydrocarbon solvent heptane to be incorporated is large and they grow slender when the amount of the aromatic hydrocarbon solvent to be incorporated is large. Besides the degree with which the second aggregation occurs on the crystals after they are washed varies with the kind of the solvent to be used and the secondary aggregation can be repressed by adding to the amount of the aliphatic hydrocarbon solvent to be incorporated. Particularly by controlling the ratio of the solvents within the range mentioned above, it is made possible to obtain crystals of zinc acrylate which hardly break, repress solidification, and allow easy disintegration of masses of secondary aggregation if any suffered to form.

The alcohols which are usable in this invention are alcohols of 1–8 carbon atoms optionally containing a branch preferably. The alcohols are methanol, ethanol, propanol, isopropanol, butanol, isobutanol, pentanol, hexanol, heptanol, and octanol. Among other alcohols mentioned above, isopropanol, butanol, isobutanol, and isopentanol are used particularly advantageously. The reason for their preference is that they facilitate the removal of water from the system by means of azeotropy. Such an alcohol as has an interfacial tension of not more than 10 dynes/cm to water is used as mixed with the aromatic hydrocarbon solvent mentioned above. The mixing ratio of the alcohol and the aromatic hydrocarbon solvent is a matter of arbitrary decision in this invention and the crystal form of zinc acrylate varies with the mixing ratio. Particularly when the amount of the alcohol to be incorporated increases, the crystals are enabled to gain in growth even in the solvent outside the process of synthetic reaction and the crystal form thereof is enabled to become so thick as to render breakage of the crystals difficult to occur. As a result, the zinc acrylate is restrained from undergoing secondary aggregation. The ratio by weight of the alcohol and the aromatic hydrocarbon solvent is preferably in the range of 10:0 to 1:9 and more preferably in the range of 10:0 to 3:7 in this invention. The reason for this range is that an addition to the weight ratio of the alcohol allows the crystals to grow and the crystal form to become so thick as to render breakage thereof difficult to occur.

Now, one mode of preferred embodiment of this invention with respect to the production of zinc acrylate will be described below.

The method of this invention obtains zinc acrylate by causing zinc oxide to react with acrylic acid and meanwhile dispersing the zinc oxide in the reaction solvent mentioned above. The solvent may allow the reaction of acrylic acid with zinc oxide to proceed in the further presence of a higher fatty acid having 12–30 carbon atoms.

Specifically, a reaction vessel furnished with a stirring device having a fully satisfactory capacity of agitation and a device for thermal treatment is charged with a prescribed amount of the solvent mentioned above and made to add zinc oxide therein as kept stirred meanwhile to prepare a suspension.

The zinc oxide is preferred to have a high degree of purity. It nevertheless may contain zinc hydroxide as an impurity. Though the amount of the zinc oxide to be added in the reaction solvent is variable with the kind of a solvent to be used, it is preferably in the range of 1–7 times, more preferably 1–5 times, and particularly preferably 1.3–4.5 times, the amount of zinc oxide as reduced to ratio by weight. If the amount of the solvent is unduly large, the excess may possibly result in degrading the purity because the unaltered reactants are localized in the upper part of the reaction solution. When the amount of the solvent is decreased, the reaction solution is enabled to increase its viscosity and consequently entail such advantages as homogenizing itself, enhancing the efficiency of agitation, and exalting the purity of zinc acrylate. Moreover, since the viscosity is raised and uniformized as well, the adhesion of the reaction solution to the agitation element during the course of kneading is lessened. If the amount of the solvent exceeds 5 times the weight of zinc oxide, the excess will result in decreasing the effect of improving the purity mentioned above. Conversely, if the amount falls short of 1 times the weight of zinc oxide, the shortage will possibly result in rendering the agitation difficult.

Subsequently, the reaction solution retained by cooling when necessary at a temperature in the range of 10–70° C., preferably 15–50° C., adds acrylic acid therein and causes it to undergo a necessary reaction to form zinc acrylate. The amount of acrylic acid to be used does not need to be particularly restricted but is only required to be enough for inducing the expected reaction with zinc oxide fully satisfactorily. It is generally in the range of 50–250 parts by weight and preferably in the range of 50–200 parts by weight based on 100 parts by weight and of zinc oxide. If the acrylic acid is used in an unduly large amount, the excess acrylic acid may be removed by distillation together with the organic solvent and the water formed by the reaction during the separation and recovery of zinc acrylate. The acrylic acid to be used in this invention may be in any of the forms possibly assumed thereby. Optionally, it may somewhat contain water. Preferably, it is in a form not diluted with water. Further, the acrylic acid may be made to contain a polymerization inhibitor such as hydroquinone or hydroquinone monomethyl ether. Incidentally, the time for adding acrylic acid and the duration of the reaction may be suitably selected within a length of time falling in the range of 0.5–10 hours, preferably 2–7 hours.

This invention may form a zinc salt of higher fatty acid in advance of the addition of acrylic acid by preparing the suspension mentioned above by dispersing zinc oxide in the reaction solvent, retaining the temperature of the suspension at a level in the range of 10–70° C., preferably 30–50° C., and meanwhile adding a higher fatty acid therein and causing it to undergo the expected reaction. In this case, the time for the addition of the higher fatty acid and the duration of the reaction may be suitably selected within a length of time falling in the range of 0.5–10 hours, preferably 1–5 hours. When the zinc acrylate is synthesized in the presence of a higher fatty acid, the amounts of the acrylic acid and the higher fatty acid to be used are adjusted so that the content of zinc acrylate may fall in the range of 60–98% by weight, preferably 70–95% by weight. More specifically, the amount of the higher fatty acid to be used does not need to be particularly restricted but is only required to be enough to induce the reaction with zinc oxide fully satisfactorily and can be decided within the range of the purpose of use of zinc acrylate. It is generally in the range of 0–150 parts by weight, preferably in the range of 10–100 parts by weight based on 100 parts by weight of zinc oxide. If the amount of the higher fatty acid to be used exceeds 150 parts by weight, the excess will bring an adverse effect of putting the characteristic properties of zinc acrylate to wastage.

As concrete examples of the higher fatty acid of 12–30 carbon atoms which is used advantageously in this invention, lauric acid, myristic acid, palmitic acid, stearic acid, behenic acid, oleinic acid, and linolic acid may be cited. These higher fatty acids may be used either singly or in the form of a mixture of two or more members. Among other higher fatty acids enumerated above, palmitic acid and stearic acid are used particularly favorably. Such a higher fatty acid may be used in its unmodified form or in the form of a solution prepared in advance by using either the same organic solvent as used in the reaction or acrylic acid. It may be otherwise used, when necessary, in the form dissolved by heating.

This invention allows the higher fatty acid to be added in the system together with an anionic surfactant or a nonionic surfactant. In this invention, the amount of the anionic surfactant or nonionic surfactant to be used does not need to be particularly restricted but is only required to be enough for enabling the reaction of zinc oxide, acrylic acid, and a higher fatty acid of 12–30 carbon atoms to proceed efficiently. Properly, it is in the range of 0–15 parts by weight, preferably 0.03–6 parts by weight, based on 100 parts by weight of the zinc oxide. When the use of such a surfactant is elected, the surfactant may be used as added in advance in the same organic solvent as used for the reaction and mixed together therein.

The zinc acrylate thus obtained may be separated and recovered from the reaction solution by a known method such as, for example, a method which comprises separating the water formed by the reaction and the organic solvent in the reaction vessel by filtration and drying the residue of the filtration at a temperature in the range of 10–70° C. When the reaction vessel happens to be a kneader blender which is furnished with a stirrer fitted with raking blades, a method which separates and recovers the zinc acrylate by keeping the reaction solution stirred in its original form and distilling it at a temperature in the range of 10–70° C., preferably 15–50° C., while reducing the pressure when necessary till the excess acrylic acid, the organic solvent, and the water formed by the reaction are expelled, and drying the residue of the distillation is adopted favorably from the point of view of simplifying the equipment. The time spent for the distillation and the drying in this case can be properly selected in the range of 1–20 hours, depending on the temperature prevalent therein.

The second aspect of this invention is directed toward zinc acrylate the crystals of which have a long axis of not less than 5 μm and an aspect ratio in the range of 1–30 and zinc acrylate the crystals of which have a long axis of not less than 5 μm, an aspect ratio in the range of 1–30, and a 50% particle diameter of not less than 6 μm. The conventional zinc acrylate has resulted from the reaction using toluene as the reaction solvent. In the reaction solution, therefore, it forms slender crystals. The crystals of zinc acrylate, owing to the slenderness of crystal form, tend to break in the reaction solution and undergo secondary aggregation after they have been dried. When the fine crystals do not undergo secondary aggregation, they are so bulky as to inconvenience their storage and transportation. In the meantime, such fine aggregates tend to solidify as under a physical pressure exerted during the course of transportation and the solidified aggregates are not easily disintegrated and, prior to actual use, are required to be released from the consolidation. The zinc acrylate contemplated by this invention is in the form of crystals having a long axis preferably not less than 5 μm and more preferably falling in the range of 5–500 μm and particularly preferably in the range of 5–100 μm, an aspect ratio preferably in the range of 1–30, more preferably 1–15, and particularly preferably 1–8, and a 50% particle diameter preferably not less than 6 μm and more preferably falling in the range of 6–100 μm and particularly preferably 10–50 μm. If the crystals are unduly fine, the excess fineness will be at a disadvantage in inducing the crystals to form aggregated clusters, fail to be uniformly kneaded with a rubber composition, manifest no satisfactory dispersibility therein, and deteriorate the working atmosphere on account of their liability to be scattered. The zinc acrylate of this invention acquires such a quality as permits repression of secondary aggregation after drying, excels in dispersibility, secures fluidity consequently, and enjoys high bulkiness enough to convenience transportation and storage. Incidentally, the long axis and the aspect ratio of the crystals of zinc acrylate indicated in the specification of the subject patent application are such numerical values as are obtained of the crystals of zinc acrylate after the crystals have been dried to a water content of not more than 0.5%.

The zinc acrylate of this invention possesses such a quality as not easily sustaining breakage because the crystals thereof are thick and long as compared with those of the zinc acrylate obtained when toluene is used as a solvent. Thus, the crystals rarely succumb to further division even when they are exposed to a physical stimulation with an ultrasonic wave for the purpose of repressing zinc acrylate from undergoing secondary aggregation after the reaction or allowing the secondarily aggregated clusters of zinc acrylate to return to their original form of crystals. This invention, therefore, is further capable of providing zinc acrylate the crystals of which have a long axis of not less than 5 μm, an aspect ratio in the range of 1–30 and a 50% particle diameter of not less than 6 μm. This crystal form can be obtained by dispersing what is obtained by the method of production according to the second aspect of this invention with an ultrasonic wave having a frequency in the range of 30–50 kHz for 15 minutes. Incidentally, the 50% particle diameter used in this invention is to be determined by the method of determination described in the working examples cited herein below.

This invention further requires the zinc acrylate after the drying mentioned above to pass a sieve opening of 1 mm at a ratio of not less than 90%, preferably not less than 92%, and particularly preferably not less than 95%. The zinc acrylate has its crystal form vary with the kind of a reaction solvent to be used and also has its crystals after the drying vary in the degree of secondary aggregation. This secondary aggregation can be discerned by the ratio of passage of the relevant crystals through a sieve opening of 1 mm. When toluene was used as the reaction solvent, the ratio of passage through a sieve opening of 1 mm was lower than 70%. This invention attains a ratio of passage of not less than 95% and this fact indicates that the zinc acrylate may well be rated as a product succumbing very rarely to secondary aggregation. The zinc acrylate of this quality can be produced by the method of production contemplated by the first aspect of this invention.

Further, the zinc acrylate of this invention has a solid disintegrating load of not more than 1.0 kg/cm$^2$, preferably not more than 0.5 kg/cm$^2$, and particularly preferably not more than 0.3 kg/cm$^2$. The solid disintegrating load, namely the load required for disintegrating the solidified mass of zinc acrylate, signifies the ease of disintegration which increases in accordance as the magnitude thereof decreases. The reason for this invention to set the solid disintegrating load at a level of not more than 1.0 kg/cm$^2$ is that the disintegration of a given solid becomes extremely difficult when this solid disintegrating load is larger than 1.0 kg/cm$^2$. Incidentally, the term "solid disintegrating load" as used in the present invention represents a magnitude determined by the method of determination described in the working example cited herein below.

The zinc acrylate of this invention is further preferred to have a degree of compaction of not more than 50%. The term "degree of compaction" as used herein means the numerical value which is obtained by testing a given sample for loose apparent relative density and solid apparent relative density and calculating the following formula using the results of the test.

Degree of compaction (%)=[100(solid apparent relative density−loose apparent relative density)]/(Solid apparent relative density)

These numerical values can be measured by a powder property measuring device made by Hosokawa Micron K. K. and sold under the model designation of "Powder Tester PT-N Type." The degree of compaction is the factor most deeply related to the rheological characteristics of powder. In the case of a zinc acrylate composition, the flowability of the composition is degraded when the degree of compaction exceeds 50% so that the composition, when left standing at rest in the hopper for a long time, will be released with unusual difficulty.

The third aspect of this invention is directed toward a zinc acrylate composition comprising the zinc acrylate of the second aspect of this invention and a zinc salt of higher fatty acid of 12–30 carbon atoms. The zinc salt of the higher fatty acid mentioned above is incorporated in the composition as a dispersing agent for zinc acrylate and this incorporation enables the zinc acrylate to secure its fluidity further. This higher fatty acid may be the same as mentioned in the first aspect of this invention. The mixing ratio of the zinc acrylate and the zinc salt of the higher fatty acid is such that the zinc salt of higher fatty acid is contained at a proportion in the range of 0–40% by weight, more preferably 5–30% by weight, and particularly desirably 10–20% by weight in the zinc acrylate composition. If this proportion to the rubber composition exceeds 40% by weight, the excess will prevent the zinc salt from being fully satisfactorily cross-linked to the butadiene rubber resulting from the addition of the zinc salt to the rubber composition. Conversely, if this proportion falls short of 5% by weight, the shortage, the effect of the added zinc salt in enhancing the flowability of zinc acrylate will not be sufficient. In the calculation of the content of the zinc salt of the higher fatty acid, when the zinc acrylate contemplated by the second aspect of this invention has been produced while the higher fatty acid is continuously added to the reaction system during the course of the production, the total amount of the zinc salt of the higher fatty acid contained in the zinc acrylate composition and the newly added or formed zinc salt of the higher fatty acid will be regarded as the content.

The zinc acrylate of this invention can be restrained from succumbing to secondary aggregation and from yielding to solidification as well. When it happens to solidify at all, the solid masses are easily disintegrated. Thus, it is enabled to secure necessary flowability at the time of its actual use. When it is kneaded as a vulcanizer in a rubber composition, therefore, it manifests excellent dispersibility. Heretofore, for the purpose of repressing the degradation of flowability by secondary aggregation, it has been customary to pulverize the produced crystals of zinc acrylate by compression, impulse, friction, or shearing. The zinc acrylate and the zinc acrylate composition according to this invention obviate the necessity for such a pulverizing treatment because they are restrained from such aggregation.

EXAMPLES

Now, this invention will be described more specifically below with reference to working examples.

Example 1

In a jacketed kneader having an inner volume of 10 L and made of SUS-316, 1,140 g of heptane was placed as a solvent and 407 g of zinc oxide was added and they were stirred together till they formed a suspension. While the inner temperature of the kneader holding the suspension was retained at a temperature in the range of 5–30° C., 739 g of acrylic acid was gradually added to the suspension over a period of three hours till the temperature reached 40° C. At 40° C., the ensuant reaction was continued for four hours. Then, while the inner pressure of the kneader was gradually lowered and the inner temperature was raised to 50° C. till the pressure reached 20 Torrs, the reaction solution was distilled for five hours to expel the reaction product and the heptane. Consequently, 1,037 g of zinc acrylate was obtained.

Figure 2:
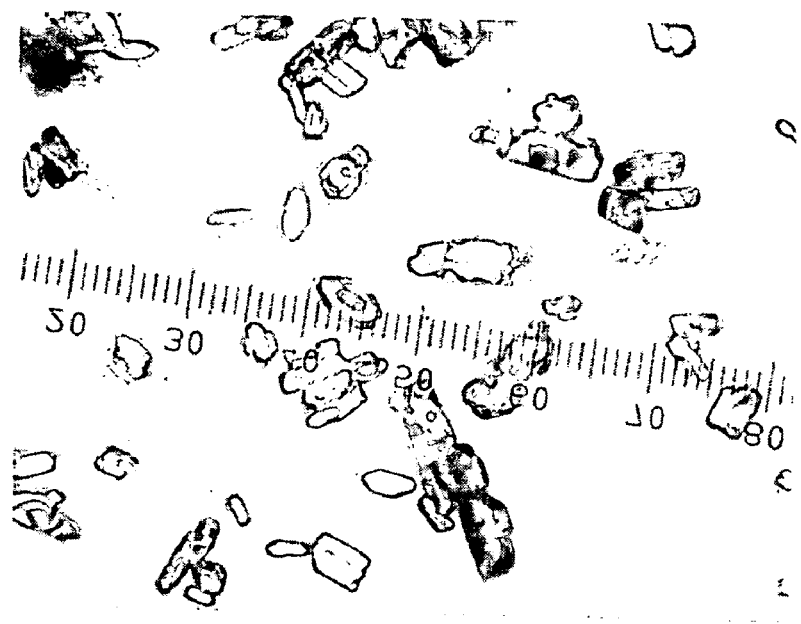
FIG. 2 is a diagram illustrating the crystal form of zinc acrylate produced in Example 1.

The crystal forms of zinc acrylate obtained before and after drying in working examples and comparative examples are shown in Table 1. The crystals of zinc acrylate after the drying were tested for long axis, aspect ration, ratio of passage through a sieve opening of 1 mm, 50% particle diameter, solid disintegrating load, and degree of compression. The results are shown in Table 2. The crystal form before the drying is shown in FIG. 2.

(Method for Determination of Solid Disintegrating Load)

The solid disintegrating load was determined by the following method depicted in FIG. 1.

First, 2 g of zinc acrylate was accurately weight out, introduced into a disk molding cylinder 1, and topped by a disk molding lid 2. A 3 kg weight 3 was left standing on the lid 2 for one hour for solidifying the sample to obtain a dislike sample 4. Then, the sample 4 was tested for disintegrating load by the use of a powder property measuring device made by Hosokawa Micron K. K. and sold under the model designation of "Powder Tester PT-N Type." The test was carried out in an aluminum bag displaced with nitrogen to prevent the same from absorbing moisture from the external environment.

(Determination of 50% Particle Diameter)

About 10 g–100 mg of a sample was dispersed in Aisopaa H with an ultrasonic wave having a frequency in the range of 30–50 kHz to prepare a dispersion medium. With the aid of a laser diffraction/scattering type particle diameter distribution tester using Aisopaa H (made by Nikkiso K. K. and sold under the trademark designation of "MICROTRAC HRA MODEL NO. 9320-x100), a given sample was tested for 50% particle diameter at a temperature of 25° C. and a humidity of 50% RH.

Example 2

Figure 3:
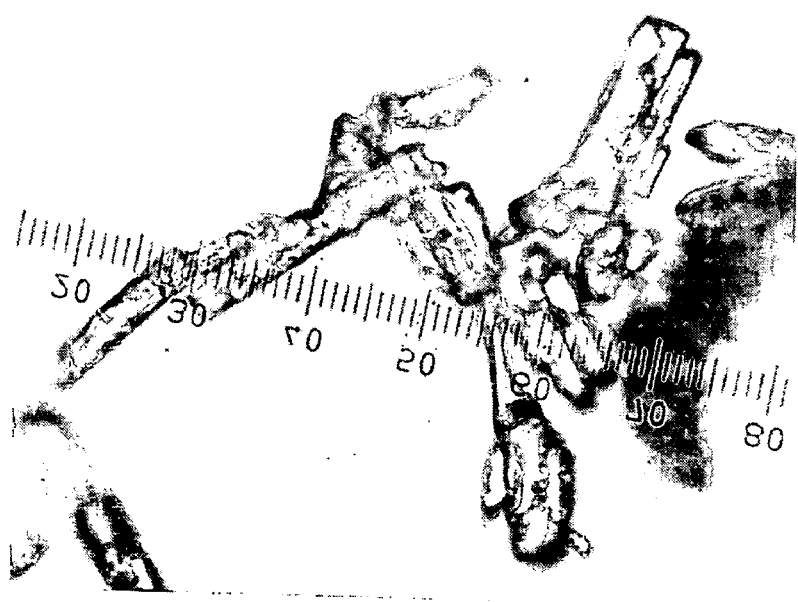
FIG. 3 is a diagram illustrating the crystal form of zinc acrylate.

Zinc acrylate was obtained by following the procedure of Example 1 while using a 4:1 mixed solvent of heptane:toluene in the place of heptane. The crystal form of zinc acrylate before drying is shown in FIG. 3.

Comparative Example 1

Figure 4:
FIG. 4 is a diagram illustrating the crystal form of zinc acrylate produced in Comparative example 1.

Zinc acrylate was obtained by following the procedure of Example 1 while using toluene in the place of heptane. The crystal form of this zinc acrylate before drying is shown in FIG. 4.

Example 3

Figure 5:
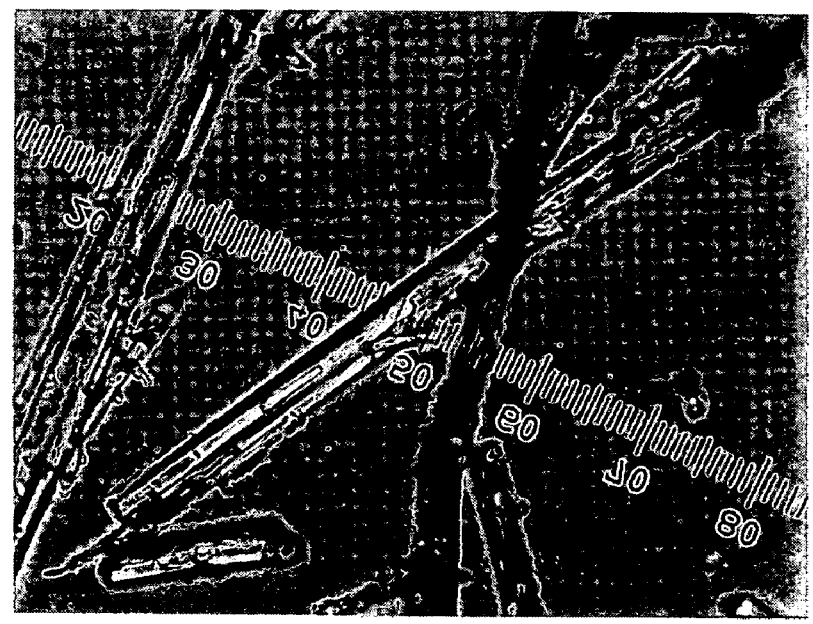
FIG. 5 is a diagram illustrating the crystal form of zinc acrylate produced in Example 4.

Zinc acrylate was obtained by following the procedure of Example 1 while using a 1:1 mixed solvent of toluene:isopropanol (IPA) in the place of heptane. The crystal form of this zinc acrylate before dying is shown in FIG. 5.

Comparative Example 2

Figure 6:
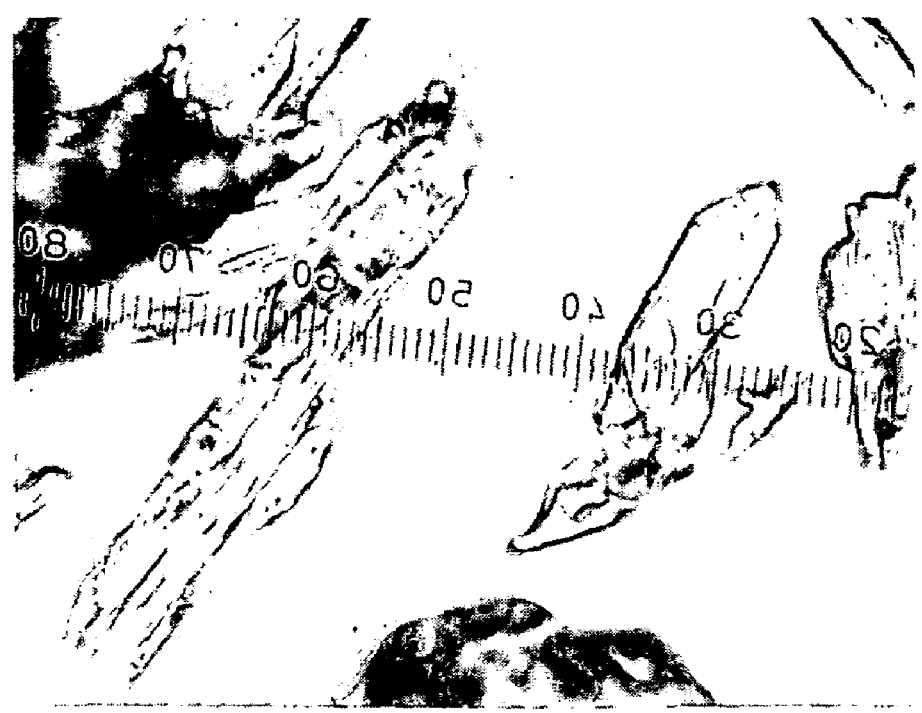
FIG. 6 is a diagram illustrating the crystal form of zinc acrylate produced in Comparative Example 2.

Zinc acrylate was obtained by following the procedure of Example 1 while using isopropanol in the place of heptane. The crystal form of this zinc acrylate before drying is shown in FIG. 6

Example 4

Zinc acrylate was obtained by following the procedure of Example 1 while using 814 g of heptane in the place of 1,140 g of heptane. The crystal form and the purity of zinc acrylate as shown in Table 3.

Example 5

Zinc acrylate was obtained by following the procedure of Example 1 while using 692 g of heptane in the place of 1,140 g of heptane.

Example 6

Zinc acrylate was obtained by following the procedure of Example 1 while using 571 g of heptane in the place of 1,140 g of heptane.

TABLE 1

| | | Crystal form ($\mu$m) | |
|---|---|---|---|
| | Solvent | Before drying | After drying |
| Example 1 | Heptane | 7 × 15 | 7 × 15 |
| Example 2 | Heptane:toluene = 4:1 | 6 × 40 | 6 × 25 |
| Comparative Example 1 | Toluene | 1 × 20 | 1 × 3 |
| Example 3 | Toluene:IPA = 1:1 | 7 × 120 | 7 × 50 |
| Comparative Example 2 | IPA | 8 × 100 | 8 × 30 |

TABLE 2

| | Solvent | Long axis of crystal ($\mu$m) | Aspect ratio | 50% Particle diameter ($\mu$m) | Ratio of passage through sieve opening of 1 mm (%) | Solid disintegrating load (kg/cm$^2$) | Degree of compaction (%) |
|---|---|---|---|---|---|---|---|
| Example 1 | Heptane | 15 | 2.1 | 11.0 | 95 | 0.2 | 39.9 |
| Example 2 | Heptane:Toluene = 4:1 | 25 | 4.2 | 20.3 | 96 | 0.3 | 39.7 |
| Comparative Example 1 | Toluene | 3 | 3 | 5.5 | 69 | 1.7 | 55.2 |
| Example 3 | Toluene:IPA = 1:1 | 50 | 7.1 | 30.5 | 96 | 0.1 | 39.9 |
| Comparative Example 2 | IPA | 30 | 3.8 | 11.8 | 96 | 0.2 | 37.4 |

TABLE 3

|  | Amount of solvent | Crystal form (μm) | Purity (%) |
|---|---|---|---|
| Example 1 | 2.8 times | 7 × 15 | 96.9 |
| Example 4 | 2.0 times | 8 × 18 | 97.4 |
| Example 5 | 1.7 times | 8 × 18 | 98.2 |
| Example 6 | 1.4 times | 8 × 18 | 98.7 |

(Results)

As shown in Table 1, sole use of heptane did not cause the produced zinc acrylate to change its crystal form before and after the drying treatment. It means that the drying treatment inflicted no breakage in the crystals. In contrast, the use of toluene which found popular use heretofore resulted in causing the crystals of zinc acrylate to sustain breakages at a plurality of points in the direction of long axis owing to the drying treatment and the crystals after the drying assumed a thin and short crystal form. The breakage in the direction of long axis by the drying treatment was observed as well in a solvent system containing IPA. Since the use of an IPA-containing solvent resulted in adding to the thickness of crystal, the crystals in this solvent eventually acquired a long-axis length 20 μm in excess of the length of the crystals of zinc acrylate formed heretofore in toluene.

The ratio of passage through a sieve opening of 1 mm shown in Table 2 approximates closely to the crystal form which the zinc acrylate product assumes when it is put to actual use and it is the numerical value that reflects the degree of secondary aggregation. When toluene was used alone, the ratio of passage was caused by secondary aggregation to fall below 90%. Since the crystals produced in this case assumed a very fine form after the drying treatment, the pulverizing treatment given thereafter to the crystals enabled the crystals to acquire the same ratio of passage through a sieve opening as the crystals obtained when other solvent was used. This invention excels in respect that it obtains zinc acrylate exhibiting an excellent ratio of passage through the sieve opening without going through such a pulverizing step.

The crystals of the zinc acrylate whose ratio of passage through a sieve opening of 1 mm (%) excessed 90% had a low solid disintegrating load (kg/cm$^2$) and, therefore, were highly vulnerable to breakage. This fact indicates that the crystals, though suffered to undergo secondary aggregation, were easily separated asunder and enabled to secure flowability. When the crystals showed a low solid disintegrating load (kg/cm$^2$), they showed a low degree of compaction and excelled in flowability.

As shown in Table 3, when the amount of the solvent was 1.4 times that of zinc oxide, the produced zinc acrylate enjoyed an exalted purity and the crystals thereof had a thick form measuring 8×18 μm.

The invention claimed is:

1. A method for the production of zinc acrylate, which comprises dispersing zinc oxide in any of (a) an aliphatic hydrocarbon solvent, (b) a mixed solvent formed between an aliphatic hydrocarbon solvent and an aromatic hydrocarbon solvent, and (c) a mixed solvent formed between an aromatic hydrocarbon solvent and an alcohol and causing acrylic acid to react with said zinc oxide in said solvent.

2. A method according to claim 1, wherein the reaction of said zinc oxide with acrylic acid in said solvent is performed in the presence of a higher fatty acid of 12–30 carbon atoms.

3. A method according to claim 1, wherein said aliphatic hydrocarbon solvent is an alkane having 6–10 carbon atoms, said alcohol is an alcohol having 1–8 carbon atoms, and said aromatic hydrocarbon solvent is toluene or xylene.

4. A method for the production of zinc acrylate, which comprises dispersing zinc oxide in solvent having an interfacial tension of 50–55 dynes/cm at 20° C. to water and causing acrylic acid to react with said zinc oxide in said solvent.

* * * * *